United States Patent [19]

Luo et al.

[11] Patent Number: 5,229,073
[45] Date of Patent: Jul. 20, 1993

[54] ONE-STEP COMPETITIVE IMMUNOASSAY FOR THE SEMIQUANTITATIVE DETERMINATION OF PLASMA LIPOPROTEIN(A)

[75] Inventors: Sheng-Chang Luo; Chandu B. Patel, both of Libertyville, Ill.

[73] Assignee: Abbott Laboratories, Abbott Park, Ill.

[21] Appl. No.: 842,935

[22] Filed: Feb. 27, 1992

[51] Int. Cl.$^5$ ............... G01N 33/543; G01N 33/558; G01N 33/577
[52] U.S. Cl. ..................... 422/56; 422/57; 422/58; 436/71; 436/514; 436/518; 436/548; 436/815; 436/825
[58] Field of Search ................ 422/56–58; 435/7.1, 970, 805; 436/518, 810, 514, 548, 815, 825

[56] References Cited

U.S. PATENT DOCUMENTS 4,059,407 11/1977 Hochstrasser ............... 435/970 X
5,141,850 8/1992 Cole et al. .................. 435/970 X Primary Examiner—Jill A. Johnston
Attorney, Agent, or Firm—Daniel R. Curry

[57] ABSTRACT

A competitive immunoassay to measure Lp(a) levels semiquantitatively and identify individuals with elevated plasma Lp(a) protein levels (greater than 7 mg/dl) who have an increase risk for coronary artery disease. The assay is useful for monitoring the effectiveness of Lp(a)-lowering drugs. The assay provides a quick, reliable, easy to use and inexpensive method to measure plasma Lp(a) level with serum, plasma or whole blood.

11 Claims, 8 Drawing Sheets

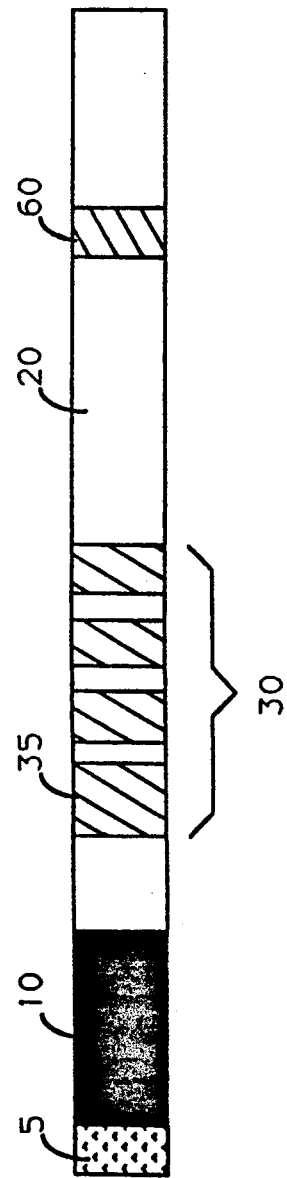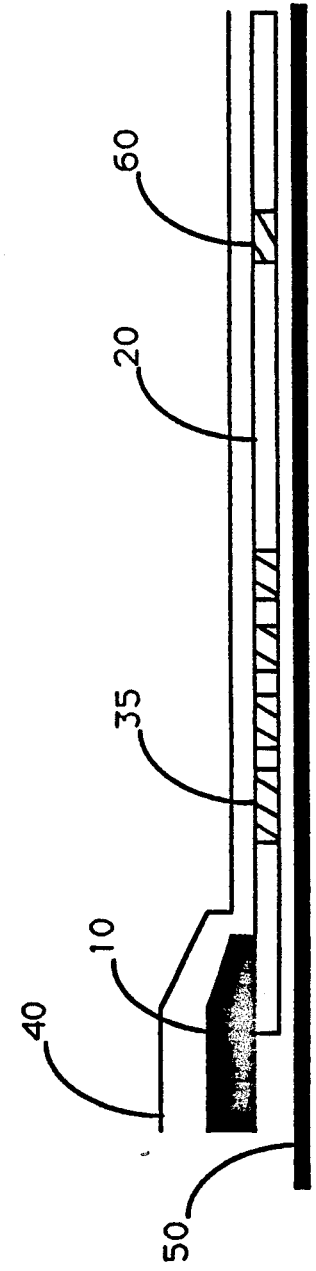
Figure 1a
Figure 1b

ONE-STEP COMPETITIVE IMMUNOASSAY FOR THE SEMIQUANTITATIVE DETERMINATION OF PLASMA LIPOPROTEIN(A)

BACKGROUND OF THE INVENTION

1. Field of the Invention

This invention relates to a method, device and reagents for the detection of plasma lipoprotein (a). In particular, the invention relates to a test strip device for use in a competitive immunoassay for the semiquantitative measurement of plasma lipoprotein (a).

2. Description of Related Art

Lipoprotein (a) [Lp(a)] was described as a genetic variant of low density lipoprotein (LDL) in 1963 (Kaare Berg, *Acta Pathol Microbiol Scand*, 59:369-381; 1963). Later, Lp(a) was found to be different from LDL in terms of lipoprotein particle composition, electrophoretic mobility, particle size and buoyant density (Rider et al., *Circulation*, 42(13):10; 1970).

After a simple disulfide reduction, the Lp(a) particle dissociates into LDL and apolipoprotein (a) [Apo(a)] molecules. This finding led to the conclusion that the Apo(a) molecule is covalently linked to Apolipoprotein B-100 (Apo B-100) by a disulfide bond (Gaubatz et al., *Journal of Biological Chemistry*, 258:4582-4589, 1983; Fless et al., *Journal of Biological Chemistry*, 259:11470-11478; 1984; Fless et al., *Journal of Biological Chemistry*, 261:8712-8718; 1986).

Recently, it has been found that the Apo(a) molecule on the Lp(a) particle has a cDNA sequence similar to that of human plasminogen (Eaton et al., *Proc Natl Acad Sci*, 84:3224-3228, 1987; McLean et al., *Nature*, 330:132-137; 1987). In the study of atherosclerosis, the Lp(a) particle has been found to cause the formation of a plaque of degenerated thickened arterial intima (i.e., atheroma) to a greater degree than does LDL (Bihari-Varga et al., *Arteriosclerosis*, 8:851-857; 1988; Collen, D., *Thromb Haemost*, 43:77-89; 1980). This may be partly due to the disturbance of the balance between thrombogenesis and fibrinolysis caused by Lp(a). In addition, high levels of Lp(a) may favor atherosclerotic plaque formation by inhibiting plasminogen activation by tissue plasminogen activator (Olofson et al., *Euro Heart*, 10:77-82, 1989; Hamsten et al., *Lancet*, 2:3-8; Jul. 4, 1987).

Numerous studies have indicated that high levels of plasma Lp(a) are strongly associated with atherosclerosis (Ellefson et al., *Mayo Clin Proc*, 46:328-332; 1971; Berg et al., *Clin Genet*, 6:230-235; 1974; Avogaro et al., *Clin Chem Acta*, 61:239-246; 1975; Dahlen et al., *Clin Genet*, 9:558-566; 1976). When the plasma Lp(a) level is above 30 milligrams/deciliter, which is equivalent to 7 milligrams/deciliter of Lp(a) protein, the relative risk of coronary atherosclerosis is raised about twofold. When LDL and Lp(a) are both elevated, the relative risk is increased to the range of fivefold (Armstrong et al., *Atherosclerosis*, 62:249-257; 1986). It has been reported that heterozygous familial hypercholesterolemia patients with high plasma Lp(a) may have developed atherosclerosis earlier than those with low plasma Lp(a) (Utermann et al. *Proc Natl Acad Sci*, 86:4171-4174; 1989). While the function of Lp(a) is unknown, a significant correlation has been established between elevated levels of plasma Lp(a) and coronary artery disease.

Lp(a) has been measured quantitatively by radioimmunoassay (Albers et al., *J Lipid Res*, 18:331-338; 1977), radial immunodiffusion (Albers et al., *Lipid*, 9:15-26; 1974), rocket immunoelectrophoresis (Gaubatz et al., *Meth Enzymology*, 129:167-186; 1986), and recently by enzyme-linked immunosorbent assay (Labeur et al., *Clin Chem*, 35(7);1380-1384; 1989; Abe et al., *Clin Chem Acta*, 177:31-41; 1988; Fless et al., *J Lipid Res*, 30:651-662; 1989). All of these previous methods have required multiple manipulations of test sample and assay reagents, complex instrumentation and/or extended time for performance. Therefore, it would be beneficial to have a rapid one-step, non-instrumented, competitive immunochromatographic method that can semiquantitatively measure plasma Lp(a) levels to facilitate the identification of individuals having an increased risk for coronary artery disease and the progression of atherosclerotic lesions.

SUMMARY OF THE INVENTION

The present invention relates to a method for detecting and quantitating Lp(a). The method is based upon a competitive immunoassay in which free Lp(a) in the test sample competes with labeled Lp(a) for binding to anti-Lp(a) antibody immobilized upon a solid phase. When compared to the commonly used sandwich assay format, the competitive assay format has unexpectedly been found to provide a more reliable and accurate measurement of Lp(a) levels. In addition, the present invention relates to a monoclonal antibody which is specific for Lp(a) but which is not significantly affected by plasminogen present in the test sample.

The assay device of the present invention is directed to a teststrip device for determining the presence or amount of Lp(a) in a test sample. The teststrip includes an application pad containing labeled Lp(a), and optionally, a specific binding member for red blood cells. The application pad receives the test sample which transports labeled Lp(a) from the application pad while the specific binding member retains, within the pad, red blood cells from the test sample. The application pad is in fluid-flow contact with a strip of a porous material having a proximal end and a distal end, through which the test sample can travel by capillary action. The porous material contains a plurality of individual capture sites containing immobilized anti-Lp(a) antibody to which the analyte and labeled Lp(a) antigen competitively bind. The first capture site retains substantially all of the labeled Lp(a) when less than a predetermined threshold amount of Lp(a) is present in the test sample. Thus, each successive capture site which retains labeled Lp(a) indicates an increased amount of Lp(a) present in the test sample. The device may optionally include an end of assay indicator site located at the distal end of the porous material, wherein the indicator site displays a detectable signal when the assay is completed.

DESCRIPTION OF THE DRAWINGS

FIGS. 1a and 1b depict the assay device of the present invention in top-view and exploded side-view.

DETAILED DESCRIPTION OF THE INVENTION

Figure 2F:
FIGS. 2a-2f depict one embodiment of the assay device of the present invention in use.
Figure 2E:
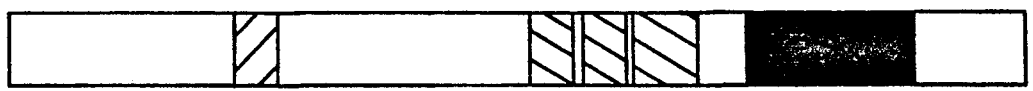
Figure 2D:
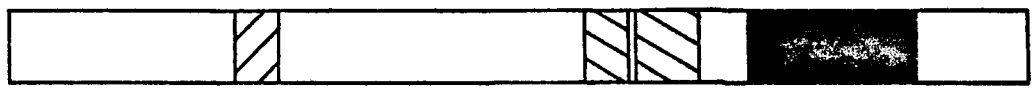
Figure 2C:
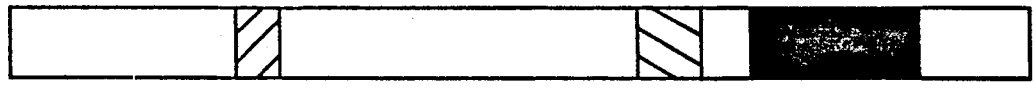
Figure 2B:
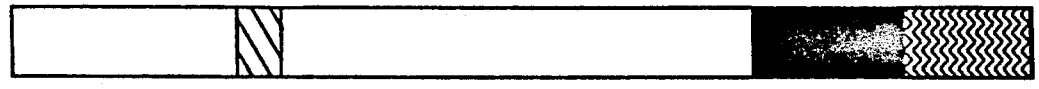
Figure 2A:
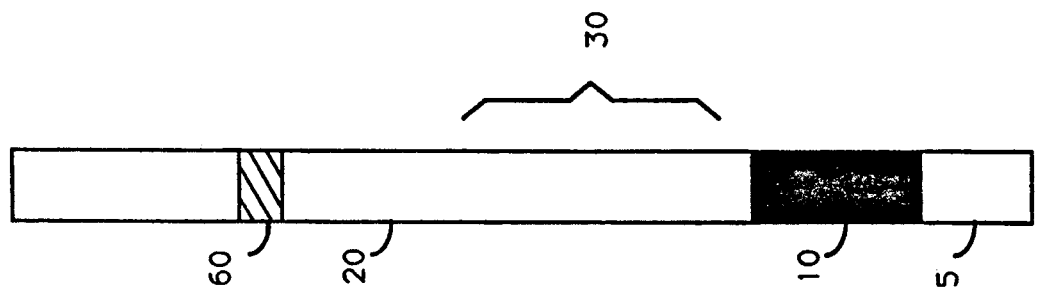

The novel Lp(a) assay of the present invention is based upon a competitive immunoassay format in which free Lp(a) in the test sample competes with labeled Lp(a) in binding to a Lp(a)-specific antibody immobilized on a solid phase. When compared with commonly used sandwich immunoassay format, the competitive assay was surprisingly found to provide a more reliable and accurate measurement of the Lp(a) level.

The protein component of Lp(a) is structurally similar to LDL because both contain apolipoprotein B-100. In addition, Lp(a) contains apolipoprotein(a) which is disulfide linked to apolipoprotein B-100. The amino acid structure of apolipoprotein(a) has been reported to have a 75% to 100% homology with serum plasminogen. The high degree of homology between apolipoprotein(a) and plasminogen suggests that Lp(a) may disturb the balance between thrombosis and fibrinolysis, and favor arterial plaque formation by inhibiting plasminogen activation of tissue plasminogen activator. Assays involving antibodies which cross react with plasminogen result in Lp(a) levels which are erroneously elevated. It is an object of the present invention to provide an antibody which binds to Lp(a) but which does not significantly cross react with LDL and plasminogen, i.e., antibodies that will not produce elevated assay results due to binding with LDL and plasminogen which may be present in the test sample.

In one embodiment, the Lp(a) assay is performed on a porous or bibulous membrane strip, and the result is determined by a visual readout of a detectable signal. Preferably, the Lp(a) in the test sample competes with labeled Lp(a) for binding to anti-Lp(a) monoclonal antibody which is immobilized on the teststrip in multiple sites. The number of capture sites that become detectable due to the immobilization of labeled Lp(a) is proportional to the amount of the Lp(a) protein present in the test sample. The novel device of the present invention has been used to semiquantitatively measure Lp(a) levels ranging from 0 to 18 milligrams/deciliter (mg/dl) of Lp(a) protein in serum, plasma or whole blood samples without the need for special separation or detection instruments. This makes the assay very useful for the quick identification of individuals with elevated levels of plasma Lp(a) (e.g., levels greater than 7 mg/dl of Lp(a) protein). Furthermore, the simple assay protocol would be advantageous for in-home use and the daily monitoring of a patient's progress when treated with Lp(a)-lowering drugs.

Published data indicate that approximately 25% of the study populations have a Lp(a) level higher than 30 mg/dl (Kostner et al. *Atherosclerosis*, 38:51; 1981). The results of conventional sandwich format enzyme immunoassays for the detection of Lp(a) suggested that about 80% of the study population had Lp(a) levels higher than 30 mg/dl and that more than 50% of test samples involved levels higher than 75 mg/dl. This may be due to the use of anti-Lp(a) antibodies which cross react with plasminogen in the sandwich assay. Testing of the same samples with the novel competitive assay format of the present invention has unexpectedly revealed that actual Lp(a) levels are lower than those measured by the sandwich assay format. The competitive assay test results of the present invention more closely resembled the levels previously measured by electroimmunoassays (Dahlen et al. *Circulation*, 74:758-765; 1986) which indicate that only 20% of the population studied had Lp(a) levels higher than 30 mg/dl of total Lp(a) mass (sum of lipid and protein of Lp(a)).

DEFINITIONS

The following definitions are applicable to the present invention.

The term "label", as used herein, refers to any substance which is attached to the Lp(a) antigen, or an analog thereof, and which is capable of producing a signal that is detectable by visual or instrumental means. Various suitable labels for use in the present invention include, but are not limited to, chromogens; catalysts; fluorescent compounds; chemiluminescent compounds; radioactive labels; direct visual labels including colloidal metallic and non-metallic particles, dye particles, enzymes or substrates, or organic polymer latex particles and liposomes or other vesicles containing signal producing substances.

A large number of enzymes suitable for use as labels are disclosed in U.S. Pat. No. 4,275,149, columns 19-23, herein incorporated by reference. A particularly preferred enzyme/substrate signal producing system useful in the present invention is the enzyme alkaline phosphatase wherein the substrate used is nitro blue tetrazolium-5-bromo-4-chloro-3-indolyl phosphate or a derivative or analog thereof.

In an alternative signal producing system, the label can be a fluorescent compound where no enzymatic manipulation of the label is required to produce a detectable signal. Fluorescent molecules such as fluorescein, phycobiliprotein, rhodamine and their derivatives and analogs are suitable for use as labels in this reaction.

In an especially preferred embodiment, a visually detectable, colored particle can be used as the label, thereby providing for a direct colored readout of the presence or concentration of the analyte in the sample without the need for further signal producing reagents. Materials suitable for use as the colored particles are colloidal metals, such as gold, and dye particles including those disclosed in U.S. Pat. Nos. 4,313,734 and 4,373,932 which are incorporated by reference herein. The preparation and use of non-metallic colloids, such as colloidal selenium particles, are disclosed in co-owned U.S. Pat. No. 4,954,452 which is incorporated by reference herein. The use of colloidal particle labels in immunochromatography is disclosed in co-owned and copending U.S. patent application Ser. No. 072,459, filed Jul. 13, 1987 which is incorporated by reference herein. Organic polymer latex particles for use as labels are disclosed in co-owned and copending U.S. patent application Ser. No. 248,858, filed Sep. 23, 1988 which is incorporated by reference herein.

The term "signal producing component", as used herein, refers to any substance capable of reacting with another assay reagent or the analyte to produce a reaction product or signal that indicates the presence of the analyte and that is detectable by visual or instrumental means. "Signal production system", as used herein, refers to the group of assay reagents that are needed to produce the desired reaction product or signal. For example, one or more signal producing components can be used to react with a label and generate the detectable signal, i.e., when the label is an enzyme, amplification of the detectable signal is obtained by reacting the enzyme with one or more substrates or additional enzymes to produce a detectable reaction product.

The term "ancillary specific binding member", as used herein, refers to any member of a specific binding pair which is used in the assay in addition to the anti-Lp(a) antibody and Lp(a) antigen and analogs and which becomes a part of the final binding complex. One or more ancillary specific binding members can be used in an assay. For example, an ancillary specific binding member can be labeled avidin which binds to a biotinylated Lp(a) antigen thereby labeling the Lp(a) antigen.

A preferred embodiment of the teststrip is shown in FIGS. 1a and 1b. An application pad (10) is attached to the top-side of porous strip (20) containing an immobilized antibody. The antibody is immobilized in a measurement region (30) which can involve a plurality of capture sites (35). Typically, the upper surfaces of the application pad and porous strip are laminated with an impermeable membrane (40), and the assembled device is attached to the top of a support material (50). Optionally, the device may include a sample loading area (5) for contacting test sample to the device. In addition, the device may optionally include an end of assay indicator (60) which produces a detectable signal upon contact with the test sample or an assay reagent.

The application pad is in fluid-flow contact with one end of the porous strip, referred to as the proximal end, such that the test sample can pass or migrate from the application pad to the porous strip. Fluid-flow contact can include physical contact of the application pad to the porous strip as well as the separation of the application pad from the porous strip by an intervening space or additional material which still allows fluid to flow between the application pad and the porous strip. Substantially all of the application pad can overlap the porous strip to enable the test sample to pass through substantially any part of the application pad to the proximal end of the porous strip. Alternatively, only a portion of the application pad might be in fluid-flow contact with the porous strip. The application pad can be any material which can transfer the test sample to the porous strip.

Materials preferred for use in the application pad include, but are not limited to, nitrocellulose, porous polyethylene and glass fiber filter paper. The application pad contains and must be compatible with one or more assay reagents either diffusively or non-diffusively attached thereto. Reagents which can be contained in the application pad include, but are not limited to, labeled reagents, ancillary specific binding members, and signal producing system components needed to produce the detectable signal. For example, in a preferred embodiment of the present invention a labeled Lp(a) protein is diffusively attached to the application pad; this eliminates the need to separately combine the test sample and the labeled reagent prior to using the device. The isolation of various assay reagents in the application pad also keeps interactive reagents separate and facilitates the manufacturing process.

The application pad receives the test sample, and the wetting of the application pad by the sample may perform two different functions. First, it will dissolve or reconstitute a predetermined amount of reagent contained by the pad. Secondly, it will initiate the transfer of both the test sample and the freshly dissolved reagent to the porous strip.

In yet another embodiment, the teststrip device can include a filtration means. The filtration means can be a separate material placed above the application pad or between the application pad and the porous strip, or the material of the application pad itself can be chosen for its filtration capabilities. The filtration means can include any filter or trapping device used to remove particles above a certain size from the test sample. For example, the filter means can be used to remove red blood cells from a sample of whole blood, such that plasma is the fluid received by the application pad and transferred to the porous strip. Such filter means are disclosed by U.S. Pat. No. 4,477,575 and WO Application No. 86/02192, published Apr. 23, 1987.

Yet another embodiment of the present invention involves the use of an additional layer or layers of porous material placed between the application pad and the porous strip or overlaying the application pad. Such an additional pad or layer can serve as a means to control the rate of flow of the test sample from the application pad to the porous strip. Such flow regulation is preferred if an extended incubation period is desired for the reaction of the test sample and the reagent(s) in the application pad. Alternatively, such a layer can contain an additional assay reagent(s) which is preferably isolated from the application pad reagent(s) until the test sample is added, or it can serve to prevent unreacted assay reagents from passing to the porous strip.

When small quantities of non-aqueous or viscous test samples are applied to the application pad, it may be necessary to employ a wicking solution, preferably a buffered wicking solution, to carry the reagent(s) and test sample from the application pad and through the porous strip. When an aqueous test sample is used, a wicking solution generally is not necessary but can be used to improve flow characteristics or adjust the pH of the test sample. The wicking solution typically has a pH range from about 5.5 to about 10.5, and more preferably from about 6.5 to about 9.5. The pH is selected to maintain a significant level of binding affinity between the specific binding members in the assay. When the label is an enzyme, however, the pH also must be selected to maintain significant enzyme activity for color development in enzymatic signal production systems. Illustrative buffers include phosphate, carbonate, barbital, diethylamine, tris, 2-amino-2-methyl-1-propanol and the like. The wicking solution and the test sample can be combined prior to contacting the application pad or they can be contacted to the application pad sequentially.

The porous strip of the assay device of the present invention can be any suitably absorbant, porous, bibulous or capillary possessing material through which a solution containing the analyte can be transported by a capillary or wicking action. Natural, synthetic, or naturally occurring materials that are synthetically modified, can be used as the porous strip including, but not limited to: cellulose materials such as paper, cellulose, and cellulose derivatives such as cellulose acetate and nitrocellulose; fiberglass; cloth, both naturally occurring (e.g., cotton) and synthetic (e.g., nylon); porous gels such as silica gel, agarose, dextran, and gelatin; porous fibrous matrixes; starch based materials, such as cross-linked dextran chains; ceramic materials; films of polyvinyl chloride and combinations of polyvinyl chloride-silica; and the like. The porous strip should not interfere with the production of a detectable signal. The porous strip should have a reasonable inherent strength, or strength can be provided by means of a supplemental support.

In one embodiment of the present invention, nitrocellulose is used as the porous strip material. When nitrocellulose is used, however, the material of the application pad should be chosen for its ability to premix the test sample and any reagent contained in the application pad, i.e., fluid-flow through a nitrocellulose membrane is laminar and does not provide the more turbulent flow characteristics which allows the initial mixing of test sample and application pad reagents within the porous strip. If nitrocellulose is used as the porous strip, then hydrophilic polyethylene or glass fiber filter paper have been found to be suitable application pad materials; such materials enable the mixing and reaction of the test sample and application pad reagents within the application pad and before transfer to the porous strip. An especially preferred application pad is glass fiber filter paper.

The particular dimensions of the porous strip will be a matter of convenience, depending upon the size of the test sample involved; the assay protocol, the means for detecting and measuring the signal, and the like. For example, the dimensions may be chosen to regulate the rate of fluid migration as well as the amount of test sample to be imbibed by the porous strip.

In the teststrip device of the present invention, the capture antibody is immobilized on the porous strip to form at least one analyte capture site, i.e., that region of the porous strip having one or more capture reagents non-diffusively attached thereto. In one embodiment of the present invention, the measurement region of the teststrip may include a plurality of capture sites containing immobilized anti-Lp(a) antibody. In addition, the different capture sites may contain different amounts of immobilized anti-Lp(a) antibody, i.e., a higher amount in the first capture site and lesser amounts in subsequent sites. For example, the first capture site, typically in the shape of a bar, can contain two micrograms of anti-Lp(a) antibody while the remaining capture sites contain one microgram of antibody.

Sandwich format enzyme immunoassays for the detection of Lp(a) are commercially available. The typical solid phase sandwich assay involves a monoclonal or polyclonal anti-Lp(a) antibody immobilized on a solid phase, and a labeled anti-Lp(a) antibody or an anti-apolipoprotein B-100 polyclonal antibody, which form a ternary complex with Lp(a) present in the test sample (Fless et al., *J Lipid Res*, 30:651-662; 1989 and Labeur et al., *Clin Chem*, 35[7]:1380-1384; 1989). To the inventors' knowledge, only one competitive enzyme immunoassay has been previously described (Gaubatz et al., *Meth Enzymology*, 129:167-186; 1986) wherein an Lp(a) antigen is immobilized on a solid phase and the test sample Lp(a) competes with the immobilized Lp(a) for binding to a labeled anti-Lp(a) antibody.

In contrast, the competitive assay of the present invention involves an anti-Lp(a) antibody immobilized on a solid phase such that free Lp(a) in the test sample can compete with a labeled Lp(a) antigen or analog for binding to the immobilized antibody. The lower the amount of detectable complex formed on the solid phase, the more Lp(a) present in the test sample. This novel assay format advantageously reduces the detection of nonspecifically bound protein associated with previously known assay formats. The anti-Lp(a) antibodies of the previously known sandwich assays typically cross-reacted with plasminogen in the test sample and thereby resulted in assay interference and inaccurate reports of elevated Lp(a) levels. Because interfering binding reactions are inhibited in the present competitive format, the present invention provides a more reliable and accurate measurement of the Lp(a) level. The present invention also advantageously uses a multiple capture site teststrip device to provide a quantitative measurement of Lp(a) without the need for a standard inhibition curve. The multi-capture site device is prepared such that if a threshold amount of Lp(a) is not present in the test sample, then substantially all of the labeled Lp(a) antigen will bind to the antibody in the first capture site and thus become immobilized in the first capture site. If a greater than threshold amount of Lp(a) is present in the test sample, the free Lp(a) will compete in binding to the immobilized antibody such that labeled Lp(a) will be displaced, in part, to a subsequent capture site on the teststrip. The greater the amount of Lp(a) in the test sample, the greater the number of capture sites that will display a detectable signal.

FIG. 2 illustrates the use of the novel teststrip device (2a) of the present invention. During the assay (2b), the test sample is applied to the loading area (5). When the end of assay indicator (60) has developed, the assay is complete. The number of capture bars in the measurement region (30) that contain immobilized label is a function of the amount of Lp(a) protein present in the test sample. The capture bars may contain different amounts of immobilized anti-Lp(a) antibody such that each successive bar or capture site that displays the detectable label is defined by a range of Lp(a) concentrations. For example, the appearance of label only at the first capture site (2c) could indicate that less than 4 mg/dl of Lp(a) was present in the test sample. The appearance of label at both the first and second capture sites (2d) could indicate that there was more than 4 but less than 7 mg/dl of Lp(a) present in the test sample. The appearance of label at the first, second and third capture sites (2e) could indicate that there was more than 7 but less than 12 mg/dl of Lp(a) present in the test sample. And, the appearance of label at the first, second, third and fourth capture sites (2f) could indicate that there was between 12 and 18 mg/dl of Lp(a) present in the test sample.

EXAMPLE

The following examples describe the novel teststrip device of the present invention as well as Lp(a) assays which were performed in accordance with the present invention.

EXAMPLE 1

Teststrip Device

Isolation of Lp(a) from Human Plasma

One unit of human plasma was collected from one liter of whole blood (Interstate Blood Bank, Milwaukee, Wis. A protease inhibitor stock solution (30 ml; 0.2M sodium EDTA, 200 mg/ml of chloramphenicol, 2.5% sodium azide, 10 mg/ml of gentamicin sulfate, 20,000 units/ml of kallikrein inactivator, 1M benzamidine and 0.2M phenylmethylsulfonylfluoride and 0.2M NaCl, pH 7.4) was added to the plasma to minimize proteolysis. Total lipoproteins were isolated by adjusting the plasma to 1.21 grams/milliliter with solid NaBr and centrifuging (in a 60Ti rotor at 59,000 rpm for 20 hours at 15° C.). Total lipoprotein fractions were then dialyzed against 0.15M NaCl, pH 7, containing 0.01% sodium EDTA, for 24 hours with three changes to remove extra salt. Total lipoproteins were further passed through an anti-Lp(a) monoclonal antibody affinity column (using 4F2 antibody as hereinafter described) which was prepared by coupling the monoclonal antibody to a solid phase (Affi-Gel 10;Bio-Rad, Richmond, Calif.). The bound Lp(a) was eluted from the affinity column (using 0.1M glycine-HCl, pH 2.8). The eluted fractions were immediately adjusted to neutral pH by adding Tris-base buffer (1M, pH 10.5). The concentration of Lp(a) was determined by a modified Lowry method (as described in Markwell et al., *Anal Biochem*, 87:206–210; 1978). The purity of the isolated Lp(a) was evaluated by 6.6% SDS-PAGE (sodium dodecyl sulfate-polyacrylamide gel electrophoresis) under reduced conditions and immunoblotting (as described in Towbin et al., *Proc Natl Acad Sci USA*, 76:4350–4354; 1979 and Kraft et al., *Arteriosclerosis*, 8:212–216; 1988). Only apolipoprotein B-100 and apolipoprotein(a) bands were observed on the stained gels.

Production of Anti-Lp(a) Monoclonal Antibody

Female BALB/c mice (8–10 weeks old, Charles River Laboratories, Portage, Mich.) were immunized four times, in two to three week intervals, with isolated Lp(a) (50 μg) which was emulsified with Ribi adjuvant (Ribi Immunochemical Research, Inc., Hamilton, Mont.). Four days after the last boosting, the mice were sacrificed, and immune spleen cells were fused with myeloma cells (SP2/0 cells, immunoglobulin non-secretory fusion partner) according to the procedure reported by Gefter et al. (*Somatic Cell Genet*. 3:231; 1977). Two to three weeks later, tissue culture spent media were collected from hybrid growing wells of microtiter plates and tested for anti-Lp(a) monoclonal antibodies. The screening procedure was carried out by the ELISA method in which culture spent media were first incubated in a Lp(a) or Apo(a)-coated microtiter plate and then incubated with a horseradish peroxidase-goat anti-mouse lg(G+M) conjugate. An enzyme substrate solution (o-phenylenediamine) was added to each well for signal development, and the microtiter plate was read at optical density 492 ($O.D._{492}$) using a microtitler plate reader.

Characterization of Lp(a)-Specific Monoclonal Antibody

Twenty-nine anti-Lp(a) monoclonal antibodies were initially selected from four cell fusions. Ten of the selected antibodies reacted with apolipoprotein B-100 (Apo B-100) on a LDL particle but not with the isolated apolipoprotein(a) component of Lp(a). Four monoclonal antibodies (8B4, 4D2, 1E1 and 4F2) having a high affinity for Lp(a) and apolopoprotein(a) [Apo(a)] were purified from mouse ascites fluid. The antibodies were further characterized in terms of Lp(a) specificity and cross-reactivity with human plasminogen, in a conventional ELISA format, as well as the ability to bind different Lp(a) isoforms in an immunoblotting assay.

Figure 3:
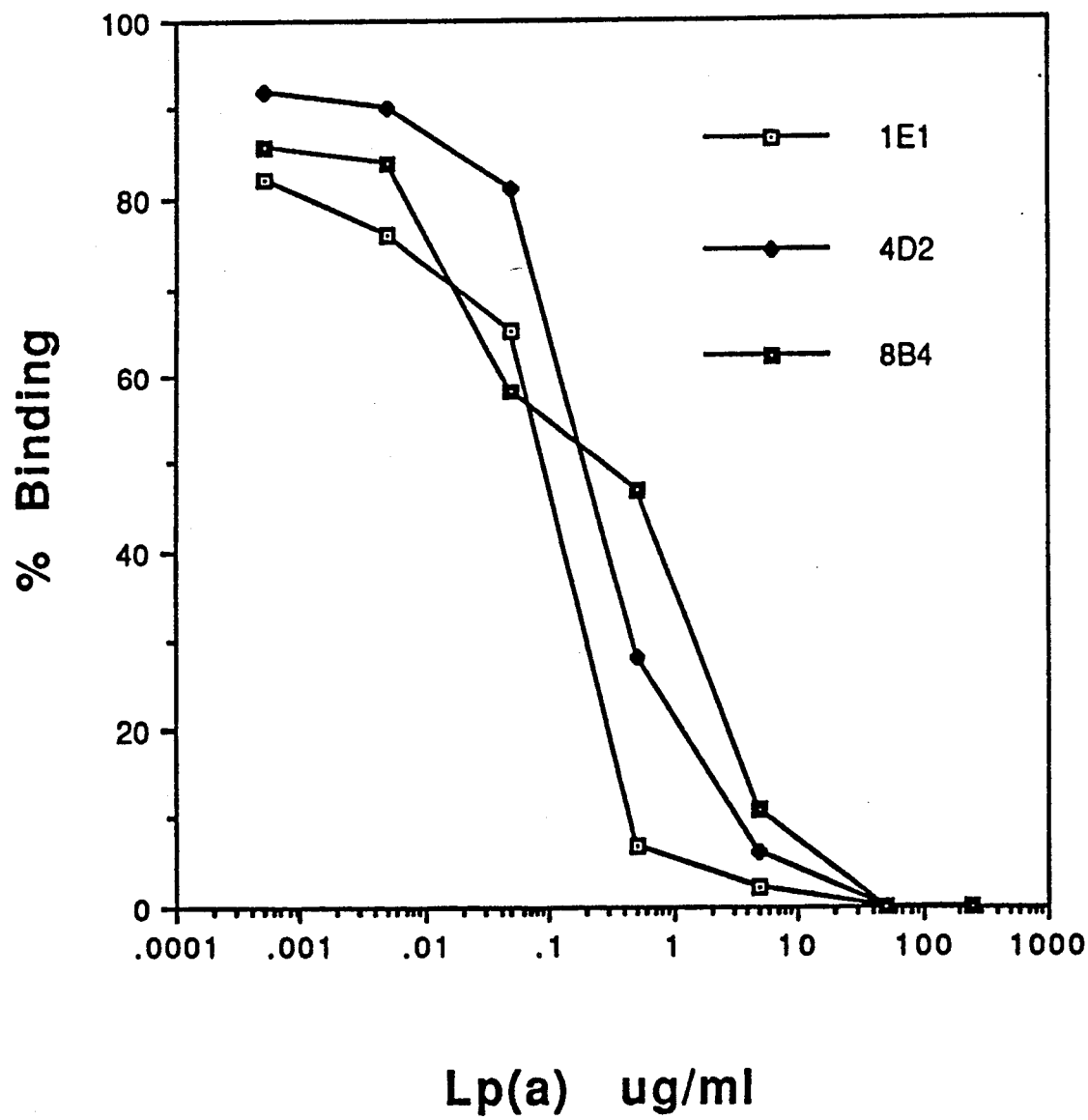
FIG. 3 depicts the results of an inhibition assay using various concentrations of Lp(a) antigen.
Figure 4:
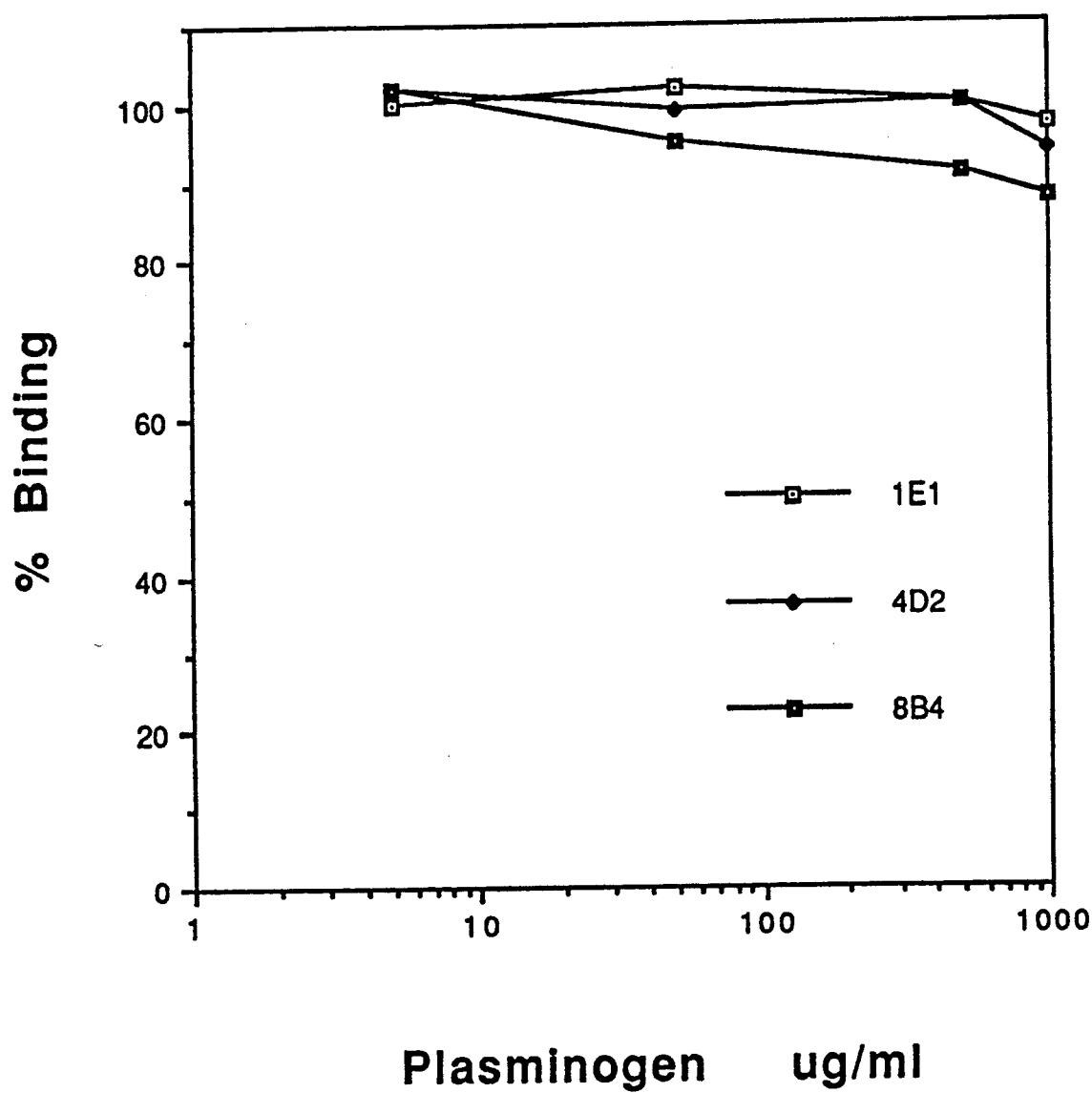
FIG. 4 depicts the results of an inhibition assay using various concentrations of plasminogen.

FIG. 3 depicts the results of an inhibition assay wherein increasing amounts of Lp(a) antigen were added to inhibit the binding between the anti-Lp(a) monoclonal antibody and Lp(a) antigen immobilized upon a solid phase. FIG. 4 depicts the results of an inhibition assay wherein increasing amounts of plasminogen were added to inhibit the binding between the anti-Lp(a) monoclonal antibody and Lp(a) antigen immobilized upon a solid phase. Free Lp(a) (0.1–0.4 μg/ml) can inhibit the binding of the monoclonal antibody to immobilized Lp(a) by 50%. In contrast, plasminogen (up to 1000 μg/ml) did not significantly inhibit the binding of the monoclonal antibody. These results indicate that the present antibodies are Lp(a) specific and do not significantly cross-react with human plasminogen.

Although Lp(a) particles have been found to float in the density range of 1.050–1.100 g/ml, each individual Lp(a) has its own density which depends on its apolipoprotein(a) content (Fless et al., *J Biol Chem*, 259:11470–11478; 1984). There are multiple isoforms of apolipoprotein(a) ranging in size from about 400,000 to 700,000 daltons. Utermann et al. (*J Clin Invest*, 80:458–465; 1987) used SDS-PAGE to show six different isoforms. Therefore, in developing an immunoassay for measuring plasma Lp(a), it is important to ensure that the antibody reagents are capable of recognizing each of the different isoforms of Lp(a). Each of the four Lp(a) monoclonals of the present invention recognized all of the different isoforms of Lp(a). Table 1 illustrates the characteristics of the monoclonal antibodies in terms of crossreactivity with plasminogen and apolipoprotein(a)-binding activity. All four clones produce IgG1 isotype of immunoglobulin.

TABLE 1

| Characteristics of Anti-Lp(a) Monoclonal Antibodies | | | | | | |
|---|---|---|---|---|---|---|
| | Reactivity in an enzyme immunoassay | | | Western Blot | | |
| Clone | Lp(a) | Apo(a) | Plasminogen | Apo(a) | Apo B-100 | Isotype |
| 8B4 | + | + | − | + | − | IgG1 |
| 1E1 | + | + | − | + | − | IgG1 |
| 4D2 | + | + | − | + | − | IgG1 |
| 4F2 | + | + | − | ND | ND | IgG1 |

Preparation of labeled Lp(a)

One milliliter of colloidal selenium sol ($O.D._{540}=150$) was adjusted to pH 8.0 by adding 50 microliters of 100 mM borate buffer, pH 8.5. Lp(a) (10 micrograms) was added to the selenium sol. The colloid mixture was then gently vortexed for two minutes. Ten percent polyethylene glycol (10 μl, M.W. 20,000) was added to the mixture to block and stabilize the Lp(a)-coated colloidal selenium. The resultant antibody/label conjugate was found to be stable in liquid form for two months and in lyophilized form for at least eight months at room temperature under low humidity.

As illustrated in FIG. 1, one embodiment of a teststrip device includes a sample loading area, an application pad, a measurement region and end of assay indicator.

Application pad

The application pad was a glass fiber material (Lydall; 0.8 cm×0.3 cm) which contained dried Lp(a)-coated colloidal selenium (Example 2, above), sheep anti-human red blood cell (RBC) antiserum and casein. The anti-RBC antiserum was used to retain RBCs in the application pad when whole blood samples were tested, thereby allowing plasma to flow into the porous membrane strip. Casein was used to aid the transport of the colloidal selenium through the strip. The application pad was prepared by saturating a piece of glass fiber material with 1.15 milliliters of conjugate (10 $O.D._{540}$ of Lp(a)-coated colloidal selenium) and a 1:50 dilution of sheep anti-RBC antiserum in a final concentration of 2% casein, 20 mM Tris buffer, pH 7.2. The application pad was frozen at $-40°$ C. for 30 minutes and then dried at 10° C. for 16 hours in a shelf lyophilizer.

Immobilization of Antibody onto Nitrocellulose Membrane

The measurement region of the assay strip was a piece of nitrocellulose membrane (approximately 5 cm × 0.3 cm) containing immobilized Lp(a)-specific monoclonal antibody (8B4) in a four bar format. A computer controlled, reagent jet was used to dispense the anti-Lp(a) monoclonal antibody reagent (4 mg/ml) in a straight line (18 cm × 0.1 cm) onto a piece of nitrocellulose membrane (5 micron; 20 cm × 15 cm) mounted on a mobile platform. The reagent jetting rate was two microliters per inch. Two jetted lines, without spacing, formed the first capture site (18 cm × 0.2 cm). The second, third and fourth capture sites were printed in a single jetted line (18 cm × 0.1 cm) with a 0.2 centimeter spacing between each site. Such a semi-quantitative assay having a multiple capture site format with visual readout had an assay range of from 0 to about 18 mg/dl of Lp(a).

End of Assay Indicator

The end of assay indicator was located at the end of the teststrip. A pH sensitive dye (quinaldine red) was used. When the pH of the quinaldine red solution was below 1.4, it was colorless. When the pH was greater than 3.2, it turned red. The 0.02% quinaldine red solution, pH 0.9, was dispensed onto the antibody immobilized nitrocellulose membrane by a reagent jet which printed a line (18 cm × 0.1 cm) located 2.5 centimeters upstream from the fourth capture site. When the plasma sample (pH > 5) was transported to the end of assay indicator, the dye turned red, thereby indicating that the assay was completed.

Assembly of the Assay Strip

The schematic assembly of the assay strip is depicted in FIG. 1. The application pad (15 cm × 0.8 cm) was attached to the top-side of the antibody immobilized nitrocellulose membrane (15 cm × 5 cm) at 0.5 centimeter downstream from the first capture site with a 0.1 centimeter junctional area. The strip was then laminated on both sides of the application pad and membrane with eight centimeter wide adhesive tape (Adhesive Research, INC, Glenrock, Pa.). The assembled application pad and membrane was then attached to the top of a clear transparency plastic film to provide mechanical support (3 M, St. Paul, Minn.) with double side adhesive tape. One centimeter of plastic film extended beyond the application pad for use as a test sample loading area. The whole assembly was cut into assay strips in the dimensions of 6 centimeters × 0.3 centimeters with a slicing cutter (Schleicher & Schuell, Keene, N.H.).

EXAMPLE 2

Assay Performance

Terumo Lp(a) ELISA

The Terumo (Elkton, Md.) Lp(a) sandwich assay was carried out according to the manufacturer's instructions. Ten microliters of sample was added to two milliliters of dilution buffer to make a 1:201 dilution. One hundred microliters of diluted sample calibrator and control were pipetted into anti-Lp(a) monoclonal antibody pre-coated wells of a microtiter plate. The plate was incubated at room temperature for one hour on a rotator. After removing the unbound portion by washing the wells, a conjugate of anti-Lp(a) antibody and horseradish peroxidase (100 microliters) was pipetted into each well. The plate was incubated at the same conditions for 20 minutes. After washing the wells, an o-phenylenediamine substrate solution (100 microliter) was added to each well and was allowed to react for 20 minutes to develop color. The enzyme reaction was stopped, and the plate was read at $O.D._{492}$. The concentration of Lp(a) in the test samples was determined by a standard calibration curve ranging from 0 to 80 mg/dl of total Lp(a) mass (sum of lipid and protein).

Competitive Assay Teststrip

Twenty-five microliters of serum of plasma, or 50 microliters of whole blood, were applied to the sample loading area of the teststrip device of the present invention (constructed substantially in accordance with the description of Example 1). The liquid portion of the test sample entered the application pad, rehydrated the Lp(a)-coated colloidal selenium and was transported to the nitrocellulose membrane strip. The Lp(a) present in the test sample competed with the Lp(a)-coated colloidal selenium conjugate for binding to the immobilized anti-Lp(a) monoclonal antibody on the capture sites of the porous membrane. When the end of assay indicator had developed, the assay was complete. The assay required about 8 to 10 minutes to complete when serum or plasma samples were used, and about 12 to 15 minutes to complete when whole blood was used as the test sample. The results of the assay were determined by observing the number of bars which displayed a detectable signal (i.e., immobilized conjugate) at the end of the assay. The number of capture bars that appeared was related to the concentration of Lp(a) protein in the sample.

Assay Dynamic Range

The dynamic range of the teststrip assay was determined by performing the assay with a series of calibrator reagents containing various amounts of purified Lp(a). Each successive capture site that become colored by the immobilization Lp(a)-coated colloidal selenium was defined by a range of Lp(a) protein concentrations. For example in one embodiment depicted in FIG. 2, when the test sample concentration of Lp(a) was less than 4 mg/dl, then substantially all of the labeled antigen would be retained in the first capture site by the immobilized anti-Lp(a) monoclonal antibody. When the sample contained an Lp(a) concentration ranging from 4 mg/dl to less than 7 mg/dl, the first two capture sites would become colored. Labeled antigen was immobilized at the third capture site when the sample contained an Lp(a) concentration above 7 mg/dl of Lp(a) protein, the level which has been suggested as indicating a high risk for coronary atherosclerosis. The dynamic ranges for the third and fourth capture sites were 7 mg/dl to 12 mg/dl and 12 mg/dl to 18 mg/dl of Lp(a), respectively. When all four capture sites are fully developed on the teststrip, the Lp(a) level in the test sample was considered to be equal to or greater than 18 mg/dl. In such instances, the Lp(a) level in the test sample may be further measured with a 1:1 dilution of the test sample. When only a partial area of a capture site developed on a teststrip, the Lp(a) concentration was estimated proportionally within the assay range of that capture bar. It will be appreciated by those skilled in the art that assay devices having different dynamic ranges could readily be constructed by modifying the amounts of immobilized antibody in the capture sites.

Accuracy

Figure 5:
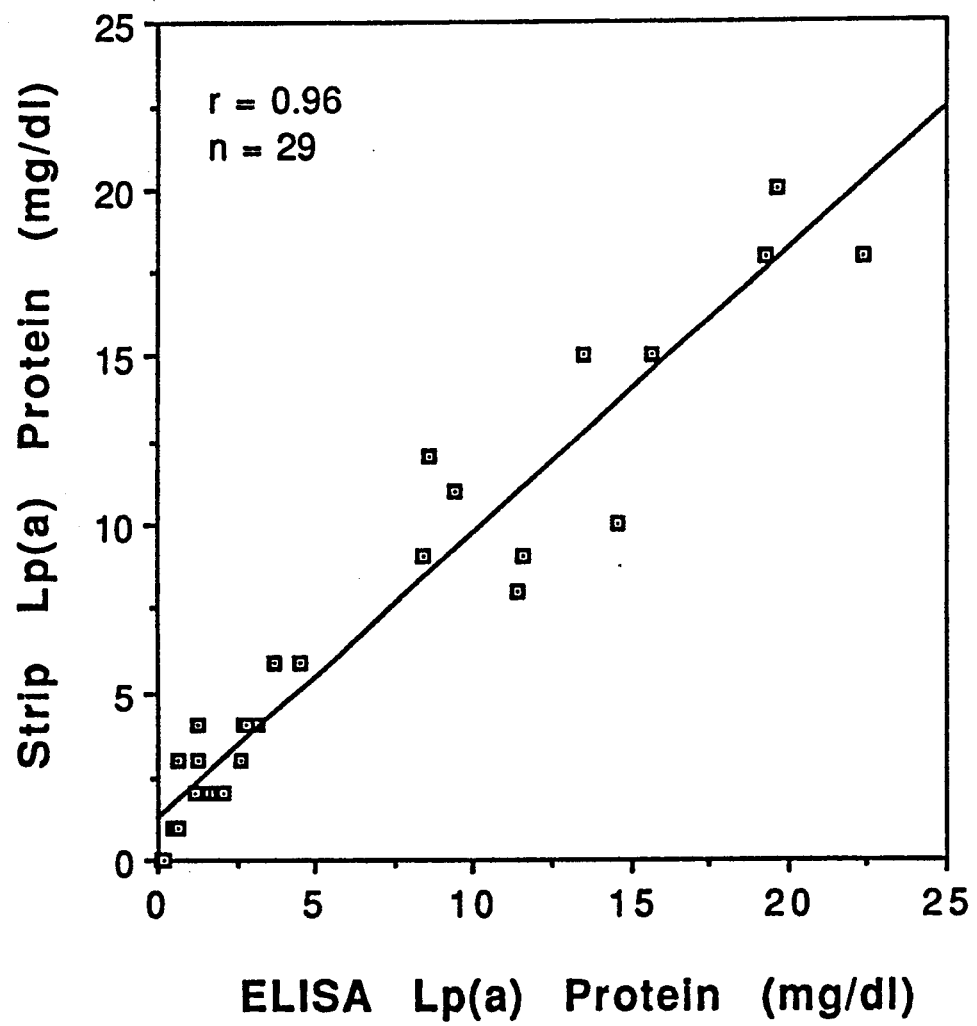
FIG. 5 depicts the assay results for 29 clinical samples comparing the performance of the competitive assay teststrip device of the present invention to a sandwich enzyme-immunoassay.
Figure 6:
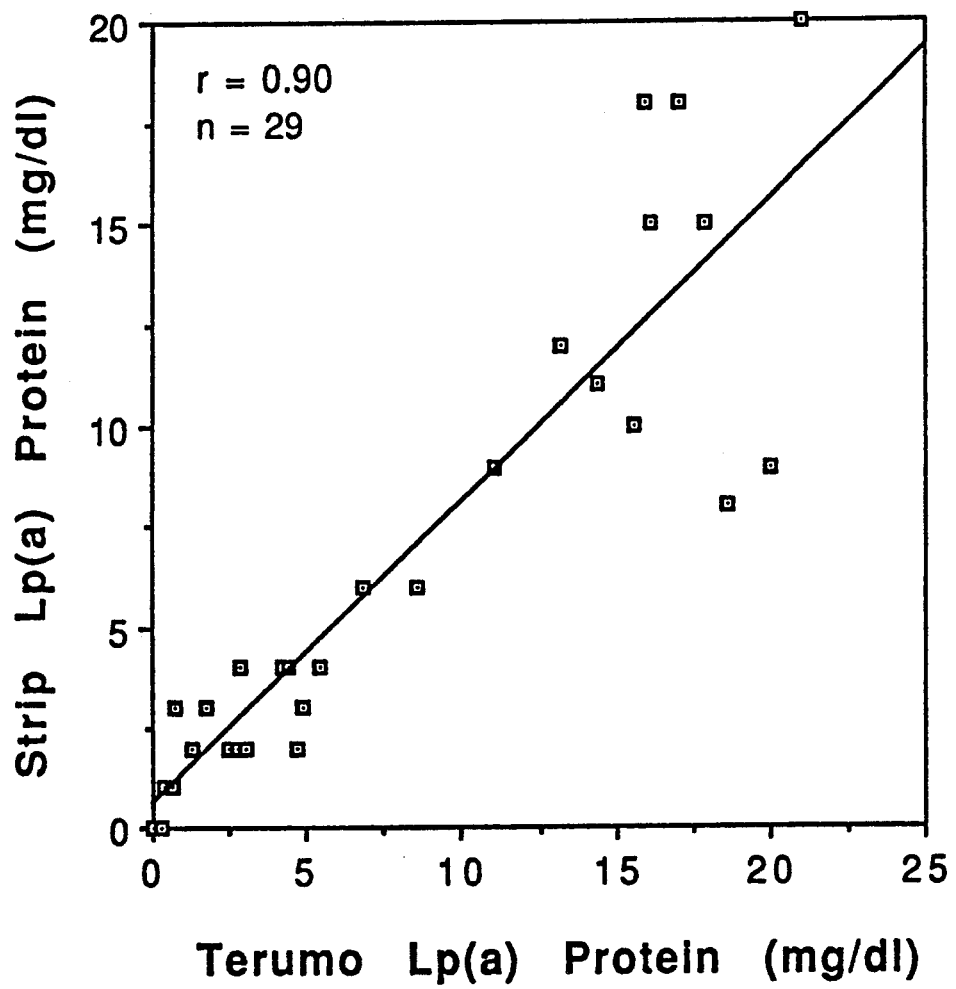
FIG. 6 depicts the assay results for 29 clinical samples comparing the teststrip device of the present invention and a Terumo enzyme-linked immunosorbent assay (ELISA).
Figure 7:
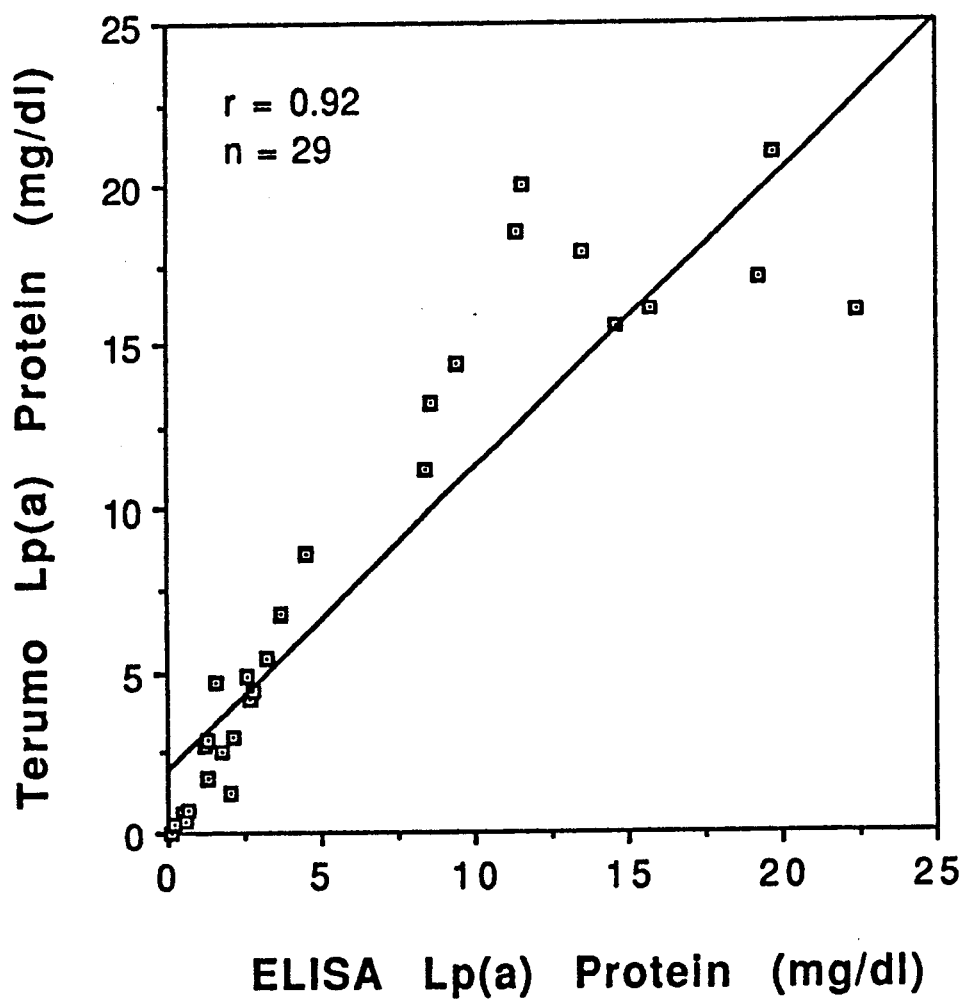
FIG. 7 depicts the assay results for 29 clinical samples comparing the enzyme-immunoassay and the Terumo ELISA.

Twenty-nine clinical samples with known lipid/lipoprotein profiles (including Lp(a) concentrations which were previously determined by an enzyme-linked immunoassay as described by Fless et al. *J Lipid Res*, 30:651-662; 1989) were tested with a teststrip device of the present invention and the Terumo ELISA. By observing the number of capture sites which became colored and the extent of the coloration, the concentration of Lp(a) in the test sample was semiquantitatively measured with the teststrip device. The assay was reproducible between-runs with the same sample. A ninety-eight percent correlation was obtained from the same set of teststrips read by two researchers. As shown in FIG. 5, the correlations of the Lp(a) teststrip assay with that of the enzyme-linked immunoassay is 96%. In order to obtain comparable units, total Lp(a) mass determined by the Terumo ELISA was divided by a conversion factor (4.2) to convert to Lp(a) protein concentration. In FIG. 6, the correlation between the teststrip assay and the Terumo ELISA is 90%. The correlation between Terumo ELISA and that of the enzyme-linked immunoassay is 92% (FIG. 7). Eleven out of 29 clinical samples (41%) with an elevated Lp(a) level (greater than 7 mg/dl) were picked up by all three methods.

Figure 8:
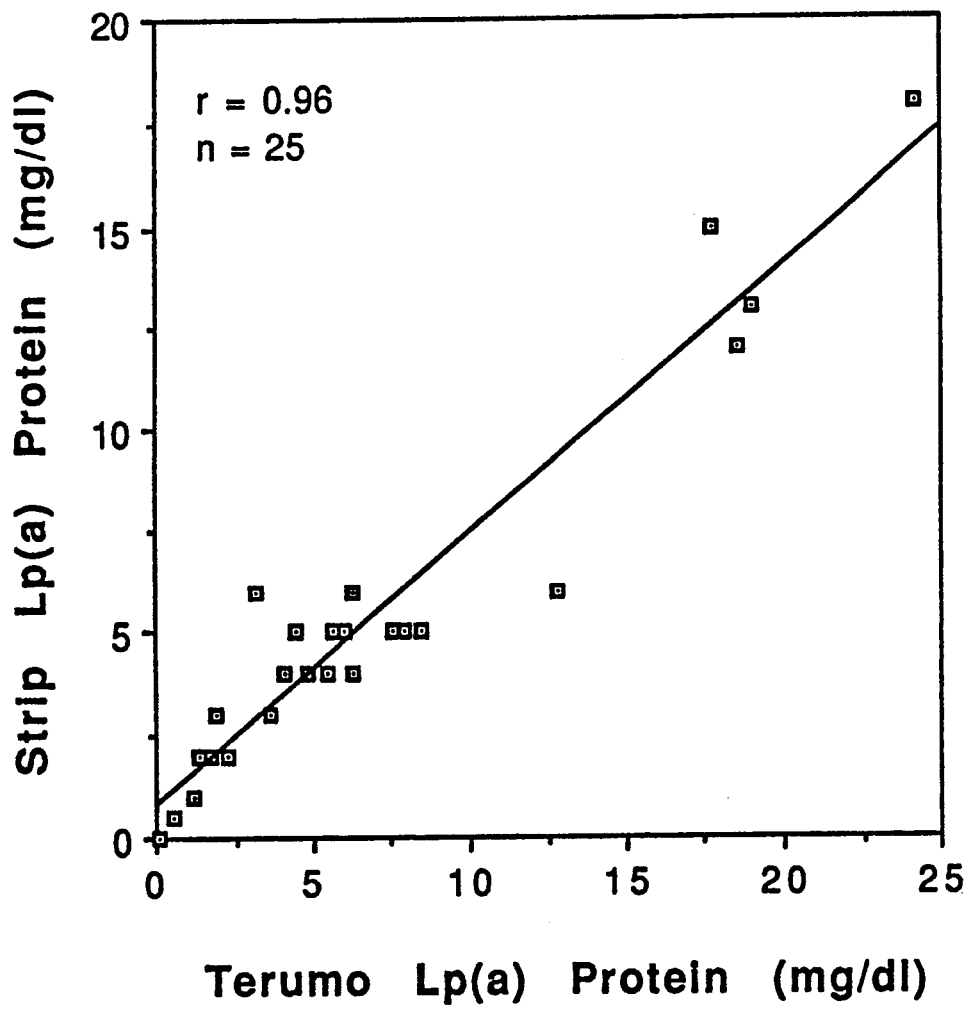
FIG. 8 depicts the assay results for 25 test samples from regular blood donors comparing the teststrip device of the present invention and a Terumo ELISA.

The correlation of the teststrip assay results, from 25 regular blood samples, with the Terumo ELISA is 96% (FIG. 8). In contrast to the 41% of the clinical samples which had elevated Lp(a) levels, only 16 to 20% of samples with elevated Lp(a) levels were observed from regular blood donors. It was observed that the Terumo ELISA method gave disproportionately higher Lp(a) measurements with the test samples that have a high Lp(a) concentration (>12 mg/dl). Overall, these results indicated that Lp(a) levels measured by the semiquantitative teststrip assay were comparable with those determined by the quantitative Lp(a) ELISA.

Interfering Substance

When up to 60 mg/dl of plasminogen was spiked into plasma, it did not interfere with the results of the assay performed with a teststrip of the present invention. This indicated that the anti-Lp(a) monoclonal antibody used as capture antibody in the assay did not cross-react with human plasminogen at its physiological levels (12 to 25 mg/dl). Clinical samples which had elevated triglyceride levels of up to 782 mg/dl, also had no significant effect on the Lp(a) teststrip assay. Plasmas collected with different anticoagulants, such as ethylenediamine tetraacetic aid and sodium citrate, provided an identical assay performance.

EXAMPLE 3

Single Site Assay Device

A teststrip device may also be constructed involving only a single capture site of immobilized anti-Lp(a) monoclonal antibody. In such a device, an instrument is used to measure the amount of labeled antigen which becomes immobilized at the capture site.

Various modifications of the present invention, in addition to those specifically presented herein, will become apparent to one of skill in the art from the foregoing description. Many of the concepts of the present invention are equally applicable to competitive assays using different antibodies, labels and/or solid phase material. In addition, the monoclonal antibodies of the present invention can be adapted for use in sandwich assay and homogeneous assay formats. The embodiments described and the alternative embodiments presented are intended as examples rather than as limitations. Thus, the description of the invention is not intended to limit the invention to the particular embodiments disclosed, but it is intended to encompass all equivalents and subject matter within the scope of the present invention as described above and as set forth in the following claims.

What is claimed is:

1. A teststrip device for determining the presence or amount of lipoprotein(a) (Lp(a)) in a test sample, comprising:
   a) an application pad containing labeled Lp(a), wherein said application pad receives the test sample, and wherein said pad is in fluid flow contact with
   b) a porous material through which the test sample migrates by capillary action, wherein said porous material contains
      a plurality of capture sites containing immobilized anti-Lp(a) antibody,
      wherein a first capture site retains substantially all of said labeled Lp(a) when there is less than a threshold amount of Lp(a) present in the test sample and through which the test sample and labeled Lp(a) must pass prior to migrating to a subsequent capture site, and
      wherein each subsequent capture site which retains labeled Lp(a) indicates that an increasingly higher amount of Lp(a) is present in the test sample.

2. The device according to claim 1, further comprising an end of assay indicator site located distal to said capture sites and containing a pH sensitive dye reactive with the test sample, wherein said indicator site displays a detectable signal when the assay is completed.

3. The device according to claim 1, further comprising a specific binding member for red blood cells in said application pad, wherein said specific binding member retains red blood cells from the test sample within said application pad.

4. The device according to claim 3, wherein said specific binding member is sheep anti-red blood cell antiserum.

5. The device according to claim 1, wherein said capture sites are separated by areas of porous materials that are substantially free of immobilized anti-Lp(a) antibody.

6. The device according to claim 1, wherein said label is a visually detectable label.

7. The device according to claim 1, wherein at least four individual capture sites of immobilized anti-Lp(a) antibody are present on said porous material.

8. The device according to claim 7, wherein a first capture site contains sufficient immobilized anti-Lp(a) antibody to retain substantially all of said labeled Lp(a) when Lp(a) in the test sample is less than 4 mg/dl of Lp(a) protein.

9. The device according to claim 7, wherein a first and second capture sites contain sufficient immobilized anti-Lp(a) antibody to retain substantially all of said labeled Lp(a) when Lp(a) in the test sample ranges from 4 mg/dl to less than 7 mg/dl of Lp(a) protein.

10. The device according to claim 7, wherein a first second and third capture site contain sufficient immobilized anti-Lp(a) antibody to retain substantially all of said labeled Lp(a) when Lp(a) in the test sample ranges from 7 mg/dl to less than 12 mg/dl of Lp(a) protein.

11. The device according to claim 7, wherein said capture sites contain sufficient immobilized anti-Lp(a) antibody to retain substantially all of said labeled Lp(a) when Lp(a) in the test sample is greater than 12 mg/dl of Lp(a) protein.

* * * * *